United States Patent
Kulstad

(10) Patent No.: US 10,335,566 B2
(45) Date of Patent: Jul. 2, 2019

(54) SYSTEMS AND METHODS FOR PROVIDING VENTILATION

(71) Applicant: Advanced Cooling Therapy, LLC, Chicago, IL (US)

(72) Inventor: Erik Kulstad, Chicago, IL (US)

(73) Assignee: ADVANCED COOLING THERAPY, INC., Chicago, IL (US)

(*) Notice: Subject to any disclaimer, the term of this patent is extended or adjusted under 35 U.S.C. 154(b) by 1280 days.

(21) Appl. No.: 14/454,873

(22) Filed: Aug. 8, 2014

(65) Prior Publication Data

US 2015/0040905 A1  Feb. 12, 2015

Related U.S. Application Data

(60) Provisional application No. 61/864,129, filed on Aug. 9, 2013.

(51) Int. Cl.
*A61M 16/00* (2006.01)
*A61M 16/10* (2006.01)
(Continued)

(52) U.S. Cl.
CPC .... *A61M 16/0069* (2014.02); *A61M 16/0051* (2013.01); *A61M 16/024* (2017.08); *A61M 16/10* (2013.01); *A61F 7/12* (2013.01); *A61M 16/0063* (2014.02); *A61M 16/04* (2013.01); *A61M 16/0465* (2013.01); *A61M 16/06* (2013.01); *A61M 16/202* (2014.02); *A61M 2016/0027* (2013.01); *A61M 2016/0039* (2013.01); *A61M 2205/3303* (2013.01);
(Continued)

(58) Field of Classification Search
CPC .......... A61M 16/0069; A61M 16/0051; A61M 16/10; A61M 16/0003; A61M 2205/3368; A61M 2205/366; A61M 2205/502; A61M 2230/202; A61M 2230/205; A61M 2230/208; A61M 2230/50; A61M 16/04; A61M 2016/0027; A61M 2210/105; A61M 2205/3344; A61F 7/12
See application file for complete search history.

(56) References Cited

U.S. PATENT DOCUMENTS 8,231,664 B2  7/2012  Kulstad et al.
8,444,684 B2  5/2013  Kulstad et al.
(Continued)

FOREIGN PATENT DOCUMENTS

WO  WO2013068918  5/2013

OTHER PUBLICATIONS

International Search Report and Written Opinion for PCT/US2014/050278 dated Dec. 16, 2014 (7 pages).
(Continued)

*Primary Examiner* — Gregory A Anderson
*Assistant Examiner* — Victoria Murphy
(74) *Attorney, Agent, or Firm* — Neal, Gerber & Eisenberg LLP; Kevin A. O'Connor

(57) ABSTRACT

Systems and methods for providing ventilation assistance or control are disclosed. Systems and methods for providing randomized ventilation are disclosed. Methods for operating a ventilation system while preventing or reducing the occurrence of ventilator associated lung injury are disclosed. Devices, systems, and methods for providing passive ventilation are disclosed.

11 Claims, 5 Drawing Sheets

(51) Int. Cl.
  *A61M 16/20* (2006.01)
  *A61M 16/04* (2006.01)
  *A61M 16/06* (2006.01)
  *A61F 7/12* (2006.01)

(52) U.S. Cl.
  CPC .............. *A61M 2205/3334* (2013.01); *A61M 2205/3344* (2013.01); *A61M 2205/3368* (2013.01); *A61M 2205/366* (2013.01); *A61M 2205/502* (2013.01); *A61M 2205/52* (2013.01); *A61M 2210/105* (2013.01); *A61M 2230/202* (2013.01); *A61M 2230/205* (2013.01); *A61M 2230/208* (2013.01); *A61M 2230/42* (2013.01); *A61M 2230/50* (2013.01)

(56) References Cited

U.S. PATENT DOCUMENTS

| | | |
|---|---|---|
| 8,523,929 B2 | 9/2013 | Kulstad et al. |
| 8,696,725 B2 | 4/2014 | Kulstad et al. |
| 8,757,152 B2 | 6/2014 | Milne et al. |
| 2003/0000526 A1* | 1/2003 | Gobel ................ A61M 16/044 128/204.18 |
| 2003/0029452 A1* | 2/2003 | Suki ..................... A61M 16/00 128/204.18 |
| 2004/0069304 A1 | 4/2004 | Jam |
| 2007/0272241 A1 | 11/2007 | Sanborn et al. |
| 2008/0295839 A1 | 12/2008 | Habashi |
| 2009/0078258 A1 | 3/2009 | Bowman et al. |
| 2011/0125053 A1 | 5/2011 | Kulstad et al. |
| 2011/0232643 A1 | 9/2011 | Mechlenburg et al. |
| 2012/0133519 A1 | 5/2012 | Milne et al. |
| 2012/0145154 A1 | 6/2012 | Baloa et al. |
| 2012/0234324 A1 | 9/2012 | Orr |
| 2012/0265172 A1 | 10/2012 | Kulstad et al. |
| 2013/0006336 A1 | 1/2013 | Kulstad et al. |
| 2013/0133654 A1 | 5/2013 | Garde et al. |

OTHER PUBLICATIONS

Extended European Search Report for European Patent Application No. 14835296.6 dated Mar. 22, 2017.

* cited by examiner

SYSTEMS AND METHODS FOR PROVIDING VENTILATION

RELATED APPLICATIONS

This application claims the priority of U.S. provisional application Ser. No. 61/864,129, filed on Aug. 9, 2013, which is incorporated by reference in its entirety.

FIELD OF THE INVENTION

The presently described technology relates to systems and methods for providing ventilation to a patient in need thereof.

BACKGROUND OF THE INVENTION

Ventilation of a patient is performed to provide oxygen to a patient's lungs while removing carbon dioxide when a patient is unable to breathe independently. Current ventilation strategies provide for control of the pressure, flow rate, or volume of gas exchanged. However, these strategies are inadequate to prevent the complications that are known to result from mechanical ventilation, including barotrauma, ventilator associated lung injury (VILI), adult respiratory distress syndrome (ARDS), and others.

As currently configured, once initial settings for ventilator parameters are provided, existing ventilation systems and strategies generally deliver a fixed volume, pressure, or flow rate repeatedly at a set rate. Certain existing ventilation systems and strategies provide for an occasional hyperinflation or "sigh" breath. However, the settings for ventilator parameters do not vary unless and until the healthcare provider manually changes the settings.

Noninvasive ventilation (NIV) has been used as an alternative to the administration of ventilatory support that utilizes an invasive artificial airway (e.g., endotracheal tube or tracheostomy tube). In certain instances, passive ventilation (e.g., holding a mask near the face or placing a nasal cannula in the nares providing passive flow of oxygen) may provide sufficient oxygen to support some patients in or nearing respiratory failure.

Accordingly, there is a need for ventilation systems and methods of operating a ventilation system that prevent or reduce the occurrence of ventilator associated lung injury and/or prevent or reduce the occurrence of repetitive alveolar distention and stress.

BRIEF SUMMARY OF THE INVENTION

At least one aspect of the present technology includes systems and methods of operating systems to provide ventilation that mimics the natural breathing patterns of non-ventilated patients by providing random attributes to the breathing cycle, such that repetitive alveolar distention and stress is reduced. The result is a more natural cycle of breaths delivered to a patient. One advantage of such systems and methods is that the occurrence of ventilator associated lung injury may be prevented or reduced. In certain embodiments, the systems and methods of the present disclosure provide a deep breath followed by a series of variably sized shallow breaths, and then by breath sizes bounded by an upper limit specified by the health care provider, in a non-repeating pattern.

At least one aspect of the present technology includes systems and methods of operating systems to provide passive ventilation through an endotracheal tube or tracheostomy tube of an invasively ventilated patient. One advantage of such systems and methods in invasively ventilated patients is that the repetitive stress on alveoli and supporting lung tissue may be reduced.

At least one aspect of the present technology includes a method of operating a ventilation system, the method including causing a ventilator to provide a random pattern of gas flow to a patient.

At least one aspect of the present technology includes a ventilation system including: one or more gas sources; one or more conduits for delivery of gas from the gas source to a patient; one or more flow regulators including one or more drive mechanisms and one or more valves; one or more operator interfaces; one or more processors; and one or more memory devices that store a plurality of instructions which, when executed by the processor, cause the processor to cause the flow regulator to deliver a random pattern of gas flow to the patient.

At least one aspect of the present technology includes a non-transitory computer readable medium including a plurality of instructions, which when executed by one or more processors of a ventilation system, cause the a processor to cause one or more flow regulators to deliver a random pattern of gas flow to a patient. In certain embodiments, the flow regulator includes a drive mechanism and/or a valve.

At least one aspect of the present technology includes a method for providing ventilation assistance or control, the method including passively delivering a volume of gas to a patient through an endotracheal tube or a tracheostomy tube.

At least one aspect of the present technology includes a system for providing ventilation assistance or control, the system including an endotracheal tube or a tracheostomy tube capable of passively delivering a volume of gas to a patient.

At least one aspect of the present technology includes a method of operating a ventilation system, the method including: (a) causing one or more processors to execute a plurality of instructions stored in one or more memory devices to operate with one or more flow regulators to deliver a volume of gas to a lung of a patient according to (i) at least one setting for one or more ventilator parameters and (ii) one or more adjustment factors; (b) causing the processor to execute the plurality of instructions to operate with one or more input devices to detect whether a physiological parameter exceeds a threshold; and (c) causing the processor to execute the plurality of instructions to vary at least one of the adjustment factors. In certain embodiments, if the physiological parameter exceeds the threshold, the adjustment factor is reduced at a default rate. In certain embodiments, if the physiological parameter does not exceed the threshold, the adjustment factor is varied randomly. In some embodiments, the flow regulator includes a drive mechanism and/or one or more valves. In some embodiments, the ventilator parameter includes: (i) tidal volume; (ii) respiratory rate; (iii) inspiratory flow rate; (iv) inspiratory-to-expiratory time ratio (I:E); and/or (v) positive end expiratory pressure. In some embodiments, the input device includes a pressure transducer. In some embodiments, the physiological parameter includes esophageal pressure. In some embodiments, the default rate is about 5%. In some embodiments, the adjustment factor is reduced at the default rate until the physiological parameter is determined to be below the threshold.

At least one aspect of the present technology includes a method of operating a ventilation system, the method including: (a) causing one or more processors to execute a plurality of instructions stored in one or more memory devices to operate with one or more flow regulators to deliver a volume of gas to a lung of a patient according to at least one setting for one or more ventilator parameters; (b) causing the processor to execute the plurality of instructions to operate with one or more operator interfaces to enable an operator to set the one or more ventilator settings; (c) causing the processor to execute the plurality of instructions to operate with the operator interface to enable the operator to set at least one criterion for a physiological parameter; (d) causing the processor to execute the plurality of instructions to operate with one or more input devices to sense the physiological parameter; and (e) causing the processor to execute the plurality of instructions to vary at least one of the settings. In certain embodiments, if the criterion is satisfied, the setting is reduced at a default rate. In certain embodiments, if the criterion is not satisfied, the setting is varied randomly. In some embodiments, the flow regulator includes one or more valves. In some embodiments, the ventilator parameter includes: (i) tidal volume; (ii) respiratory rate; (iii) inspiratory flow rate; (iv) inspiratory-to-expiratory time ratio (I:E); and/or (v) positive end expiratory pressure. In some embodiments, the input device includes a pressure transducer. In some embodiments, the physiological parameter includes esophageal pressure. In some embodiments, the criterion includes esophageal pressure less than about 25 cm $H_2O$. In some embodiments, the default rate is about 5%.

At least one aspect of the present technology includes a non-transitory computer readable medium including a plurality of instructions which, when executed by a processor, cause the processor to: (a) operate with a flow regulator to deliver a volume of gas to a lung of a patient according to (i) one or more ventilator settings and (ii) one or more adjustment factors; (b) operate with an input device to detect whether a physiological parameter exceeds a threshold; and (c) vary at least one of the adjustment factors. In certain embodiments, if the physiological parameter exceeds the threshold, the adjustment factor is reduced at a default rate. In certain embodiments, if the physiological parameter does not exceed the threshold, the adjustment factor is varied randomly.

At least one aspect of the present technology includes a non-transitory computer readable medium including a plurality of instructions which, when executed by a processor, cause the processor to: (a) operate with a flow regulator to deliver a volume of gas to a lung of a patient according to one or more ventilator settings; (b) operate with an operator interface to enable an operator to set the one or more ventilator settings; (c) operate with the operator interface to enable the operator to set at least one criterion for a physiological parameter; (d) operate with an input device to detect the physiological parameter; and (e) vary at least one of the one or more ventilator settings. The In certain embodiments, if the criterion is satisfied, the ventilator setting is reduced at a default rate. In certain embodiments, if the criterion is not satisfied, the ventilator setting is varied randomly.

At least one aspect of the present technology includes a system for providing ventilation assistance or control, the system including: (a) at least one processor; (b) at least one operator interface configured to provide input to the processor; and (c) at least one memory. The system is configured to: (i) receive a first setting for a ventilator parameter and a criterion for a physiological parameter; (ii) cause a first volume of gas to be delivered to a patient in accordance with the first setting; (iii) obtain a measured value for the physiological parameter; (iv) determine whether the measured value satisfies the criterion; and (v) cause a second volume of gas to be delivered to a patient. In certain embodiments, the second volume of gas is delivered in accordance with (1) a randomized setting or (2) a corrected setting. In some embodiments, the system is configured to apply a random value to the first setting to obtain the randomized setting. In some embodiments, the system is configured to apply a correction factor to the first setting to obtain the corrected setting. In some embodiments, the second volume of gas is delivered in accordance with a randomized setting if the measured value satisfies the criterion. In some embodiments, the second volume of gas is delivered in accordance with a corrected setting if the measured value does not satisfy the criterion. In some embodiments, the ventilator parameter includes tidal volume. In some embodiments, the physiological parameter includes esophageal pressure.

At least one aspect of the present technology includes a method for providing ventilation assistance or control, the method including: (a) receiving a first setting for a ventilator parameter and a criterion for a physiological parameter; (b) causing a first volume of gas to be delivered to a patient in accordance with the first setting; (c) obtaining a measured value for the physiological parameter; (d) determining whether the measured value satisfies the criterion; and (e) causing a second volume of gas to be delivered to a patient. In certain embodiments, the second volume of gas is delivered in accordance with (i) a randomized setting or (ii) a corrected setting. In some embodiments, the method further includes applying a random value to the first setting to obtain the randomized setting. In some embodiments, the method further includes applying a correction factor to the first setting to obtain the corrected setting. In some embodiments, the second volume of gas is delivered in accordance with a randomized setting if the measured value satisfies the criterion. In some embodiments, the second volume of gas is delivered in accordance with a corrected setting if the measured value does not satisfy the criterion. In some embodiments, the ventilator parameter is tidal volume. In some embodiments, the physiological parameter is esophageal pressure.

At least one aspect of the present technology includes a system for providing ventilation assistance or control, the system including: (a) at least one processor; (b) at least one operator interface configured to provide input to the processor; and (c) at least one memory. The system is configured to: (i) receive an operator generated ventilator setting and a first correction factor; (ii) receive a criterion for a physiological parameter; (iii) obtain a measured value for the physiological parameter; (iv) determine whether the measured value satisfies the criterion; and (v) cause a volume of gas to be delivered to a patient. In some embodiments, the system enables the volume of gas to be delivered according to an automatically adjusted ventilator setting. In some embodiments, the system is configured to obtain the automatically adjusted ventilator setting by applying the first correction factor to the operator generated ventilator setting. In some embodiments, the system is configured to obtain the automatically adjusted ventilator setting by applying a random value to the operator generated ventilator setting. In some embodiments, if the measured value satisfies the criterion, the automatically adjusted ventilator setting is obtained by application of a random value to the operator generated ventilator setting. In some embodiments, the system is configured to adjust the first correction factor to obtain a second correction factor if the measured value does not satisfy the criterion. In some embodiments, the system is configured to obtain the automatically adjusted ventilator setting by application of the second correction factor to the operator generated ventilator setting. In some embodiments, if the measured value does not satisfy the criterion, the automatically adjusted ventilator setting is obtained by adjustment of the first correction factor to obtain a second correction factor and application of the second correction factor to the operator generated ventilator setting. In some embodiments, the physiological parameter is esophageal pressure.

At least one aspect of the present technology includes a method for providing ventilation assistance or control, the method including: (a) receiving an operator generated ventilator setting and a first correction factor; (b) receiving a criterion for a physiological parameter; (c) obtaining a measured value for the physiological parameter; (d) determining whether the measured value satisfies the criterion; and (e) causing a volume of gas to be delivered to a patient. In some embodiments, the system enables the volume of gas to be delivered according to an automatically adjusted ventilator setting. In some embodiments, the method further includes obtaining the automatically adjusted ventilator setting by applying the first correction factor to the operator generated ventilator setting. In some embodiments, the method further includes obtaining the automatically adjusted ventilator setting by applying a random value to the operator generated ventilator setting. In some embodiments, if the measured value satisfies the criterion, the automatically adjusted ventilator setting is obtained by applying a random value to the operator generated ventilator setting. In some embodiments, the method further includes adjusting the first correction factor to obtain a second correction factor if the measured value does not satisfy the criterion. In some embodiments, the method further includes obtaining the automatically adjusted ventilator setting by applying the second correction factor to the operator generated ventilator setting. In some embodiments, if the measured value does not satisfy the criterion, the automatically adjusted ventilator setting is obtained by adjusting the first correction factor to obtain a second correction factor and applying the second correction factor to the operator generated ventilator setting. In some embodiments, the physiological parameter includes esophageal pressure.

DETAILED DESCRIPTION OF THE INVENTION

Figure 1:
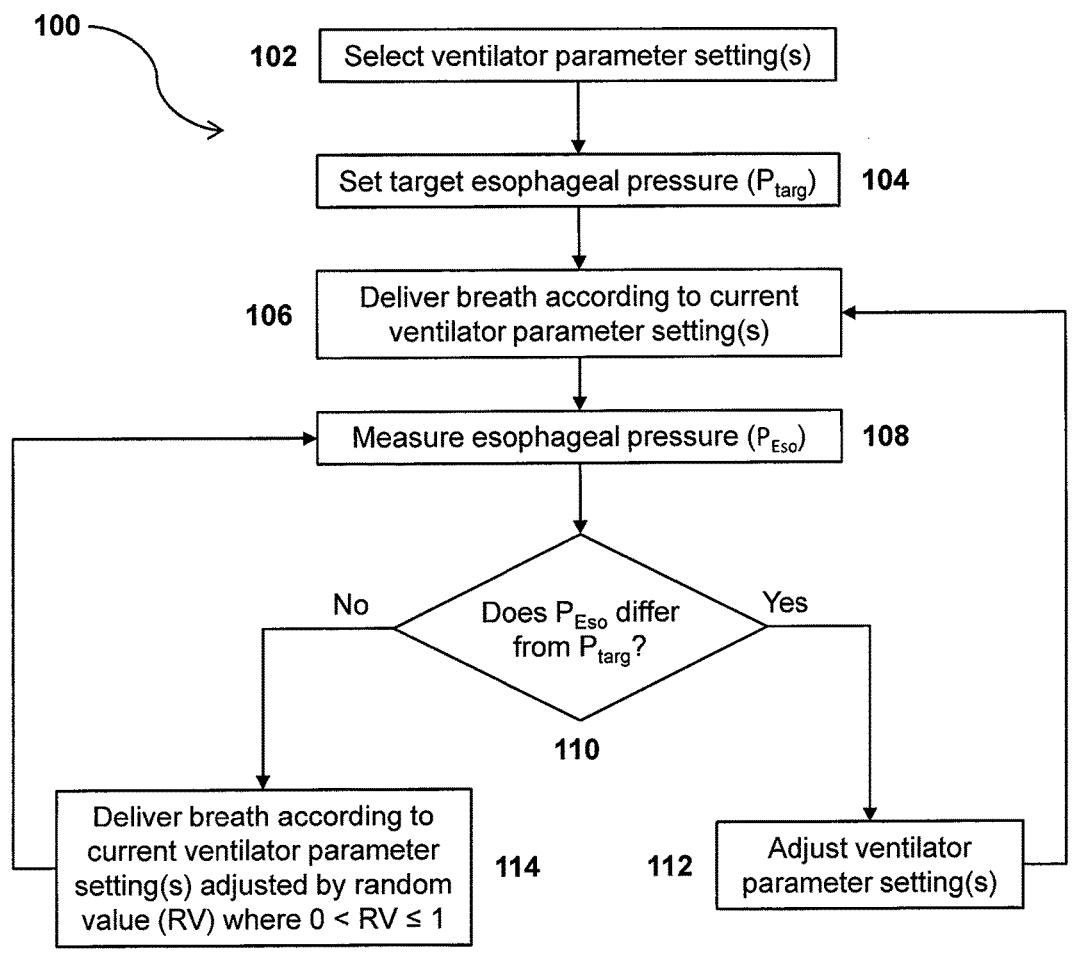
FIG. 1 shows a flowchart of one embodiment of the present technology.

The present technology provides a method of operating a ventilation system. In certain embodiments, the method includes enabling a processor to receive at least one setting for one or more ventilator parameters. In certain embodiments, the method includes enabling a processor to receive at least one criterion for one or more physiological parameters, such as pressure. In certain embodiments, the method includes delivering a breath or a series of breaths based on the ventilator parameters. In certain embodiments, the method also includes measuring the physiological parameter after delivery of the breath or series of breaths. In certain embodiments, the method includes determining whether the measured physiological parameter satisfies the criterion. In certain embodiments, the method also includes (i) delivering a subsequent breath or series of breaths based on the ventilator parameters adjusted by a random value and/or (ii) adjusting one or more of the ventilator parameters by a default amount and delivering a subsequent breath or series of breaths based on the adjusted ventilator parameters. In certain embodiments, the method includes enabling a processor to receive at least one setting for one or more ventilator parameters; enabling a processor to receive at least one criterion for one or more physiological parameters, such as pressure; delivering a breath or a series of breaths based on the ventilator parameters; measuring the physiological parameter after the breath or a series of breaths has been delivered; determining whether the measured physiological parameter satisfies the criterion; and, (i) if the measured physiological parameter satisfies the criterion, delivering a subsequent breath or series of breaths based on the ventilator parameters adjusted by a random value, or (ii) if the measured physiological parameter does not satisfy the criterion, adjusting one or more of the ventilator parameters by a default amount and delivering a subsequent breath or series of breaths based on the adjusted ventilator parameters.

The present technology provides a method of operating a ventilation system. In certain embodiments, the ventilation system receives at least one setting for one or more ventilator parameters. In certain embodiments, the ventilation system receives at least one criterion for one or more physiological parameters, such as pressure. In certain embodiments, the ventilation system delivers a breath or a series of breaths based on the ventilator parameters. In certain embodiments, the ventilation system also measures the physiological parameter after delivery of the breath or series of breaths. In certain embodiments, the ventilation system determines whether the measured physiological parameter satisfies the criterion. In certain embodiments, the gaming system also (i) delivers a subsequent breath or series of breaths based on the ventilator parameters adjusted by a random value and/or (ii) adjusts one or more of the ventilator parameters by a default amount and delivering a subsequent breath or series of breaths based on the adjusted ventilator parameters. In certain embodiments, the ventilation system receives at least one setting for one or more ventilator parameters; receives at least one criterion for one or more physiological parameters, such as pressure; delivers a breath or a series of breaths based on the ventilator parameters; measures the physiological parameter after the breath or a series of breaths has been delivered; determines whether the measured physiological parameter satisfies the criterion; and, (i) if the measured physiological parameter satisfies the criterion, delivers a subsequent breath or series of breaths based on the ventilator parameters adjusted by a random value, or (ii) if the measured physiological parameter does not satisfy the criterion, adjusts one or more of the ventilator parameters by a default amount and delivers a subsequent breath or series of breaths based on the adjusted ventilator parameters.

The present technology provides a method of operating a ventilation system. In certain embodiments, the method includes enabling a processor to receive at least one setting for one or more ventilator parameters. In certain embodiments, the method also includes enabling a processor to receive at least one setting for one or more correction factors. In certain embodiments, the method includes enabling a processor to receive at least one criterion for one or more physiological parameters, such as pressure. In certain embodiments, the method includes delivering a breath or a series of breaths based on the ventilator parameters and the correction factor(s). In certain embodiments, the method also includes measuring the physiological parameter after delivery of the breath or series of breaths. In certain embodiments, the method includes determining whether the measured physiological parameter satisfies the criterion. In certain embodiments, the method also includes (i) delivering a subsequent breath or series of breaths based on the ventilator parameters and the correction factor(s), further adjusted by a random value and/or (ii) adjusting the correction factor by a default amount and delivering a subsequent breath or series of breaths based on the ventilator parameters and the adjusted correction factor. In certain embodiments, the method includes enabling a processor to receive at least one setting for one or more ventilator parameters; enabling a processor to receive at least one setting for one or more correction factors; enabling a processor to receive at least one criterion for one or more physiological parameters, such as pressure; delivering a breath or a series of breaths based on the ventilator parameters and the correction factor(s); measuring the physiological parameter after the breath or a series of breaths has been delivered; determining whether the measured physiological parameter satisfies the criterion; and, (i) if the measured physiological parameter satisfies the criterion, delivering a subsequent breath or series of breaths based on the ventilator parameters and the correction factor(s), further adjusted by a random value, or (ii) if the measured physiological parameter does not satisfy the criterion, adjusting the correction factor by a default amount and delivering a subsequent breath or series of breaths based on the ventilator parameters and the adjusted correction factor.

In certain embodiments, ventilator parameters include the mode of operation of the ventilator, such as continuous mandatory ventilation (CMV); assist control (A/C); intermittent mandatory ventilation (IMV); synchronized intermittent mandatory ventilation (SIMV); airway pressure release ventilation (APRV); pressure support ventilation (PSV); or high frequency oscillatory ventilation (HFOV). In certain embodiments, ventilator parameters include volume, pressure, and/or flow parameters such as tidal volume ($V_T$); positive end expiratory pressure (PEEP); inspiratory flow rate ($F_I$); inspiratory-to-expiratory ratio (I:E ratio); fraction of inspired oxygen ($FiO_2$); or respiratory rate. In certain embodiments, the ventilator parameter is $V_T$.

For example, in certain embodiments, the system enables an operator, such as a healthcare provider or caregiver, to set a $V_T$ from about 4 to about 8 milliliters per kilogram of ideal body weight (ml/kgIBW), including about 5, about 6, and about 7 ml/kgIBW. In certain embodiments, the system enables an operator to set the $V_T$ to 6 ml/kgIBW or 8 ml/kgIBW. In certain embodiments, the system enables an operator to set a $V_T$ from about 200 cc to about 1000 cc, including about 300, about 400, about 500, about 600, about 700, about 800, and about 900 cc. In certain embodiments, the system enables an operator to set the $V_T$ to 500 cc. As another example, the system enables an operator to set a respiratory rate of about 8 to about 20 breaths per minute (bpm), including about 9, about 10, about 11, about 12, about 13, about 14, about 15, about 16, about 17, about 18, and about 19 bpm. In certain embodiments, the system enables an operator to set the respiratory rate to 8, 10, 12, or 16 bpm. In still another example, the system enables an operator to set a PEEP from about 2 to about 24 cm $H_2O$, including about 3, about 4, about 5, about 6, about 7, about 8, about 9, about 10, about 11, about 12, about 13, about 14, about 15, about 16, about 17, about 18, about 19, about 20, about 21, about 22, and about 23 cm $H_2O$. In some embodiments, the system enables an operator to set a PEEP of greater than 3 cm $H_2O$, greater than 5 cm $H_2O$, greater than 8 cm $H_2O$, or greater than 10 cm $H_2O$. In certain embodiments, the system enables an operator to set the PEEP to 4 or 5 cm $H_2O$. In yet another example, the system enables an operator to set an FI from about 5% to about 100%, including about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%. In some embodiments, the system enables an operator to set an $F_I$ of less than 100% or less than 50%. In certain embodiments, the system enables an operator to set the $F_I$ to 100%. In yet another example, the system enables an operator to set an I:E ratio of about 1:1, about 1:2, about 1:3, about 1:4, about 1:5, or about 1:6. In certain embodiments, the system enables an operator to set the I:E ratio to 1:2 or 1:4. During a ventilation method, the system enables one or more settings for the ventilator parameters to be adjusted manually or automatically, as further described below.

In certain embodiments, the system applies one or more correction factors to the ventilator parameter to obtain a correction-factor-adjusted ventilator parameter. In certain embodiments, the system enables an operator to set an initial correction factor. In certain embodiments, the system adjusts the correction factor automatically. In certain embodiments, the system enables an operator to adjust the correction factor. In certain embodiments, the correction factor is, for example, any number between 0 and about 1.5, including about 0.1, about 0.2, about 0.3, about 0.4, about 0.5, about 0.6, about 0.7, about 0.8, about 0.9, about 1.0, about 1.1, about 1.2, about 1.3, and about 1.4. In certain embodiments, the correction factor is a number between about 0.20 and about 1.25, including about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1.00, about 1.05, about 1.10, about 1.15, and about 1.20. In certain embodiments, the correction factor is 1. For example, in certain embodiments, the system enables the operator to set the correction factor at 1. During a ventilation method, the system enables the correction factor to be adjusted manually or automatically, as further described below.

In certain embodiments, the method includes delivering a breath or a series of breaths based on the ventilator parameter setting and, optionally, one or more correction factors. In certain embodiments, the processor of the system applies one or more correction factors to a ventilator parameter setting to obtain a correction-factor adjusted ventilator parameter. For example, in certain embodiments, the processor calculates a correction-factor adjusted ventilator parameter setting based on the ventilator parameter setting selected by an operator and a correction factor set by an operator. In one embodiment, if the processor receives input from an operator that sets $V_T$ to 500 cc and the correction factor to 0.8, the processor calculates a correction-factor-adjusted $V_T$ of 400 cc.

In certain embodiments, the method includes sensing or measuring one or more physiological parameters. In certain embodiments, the system enables one or more physiological parameters to be sensed or measured after a breath or a series of breaths has been delivered to the patient. For example, in certain embodiments, an input device is coupled to the patient to sense and/or measure a physiological parameter. In certain embodiments, the system enables one or more physiological parameters to be assessed prior to and/or following the initiation of the ventilation method. In certain embodiments, the physiological parameters include pressure, such as esophageal pressure, alveolar pressure, intrapleural pressure, or transpulmonary pressure. In certain embodiments, the physiological parameters include data that can be obtained from an arterial blood gas (ABG) test, such as pH, arterial oxygen pressure ($PaO_2$), arterial oxygen saturation ($SaO_2$), arterial carbon dioxide pressure ($PaCO_2$) or surrogates thereof, such pulse oximeter oxygen saturation ($SpO_2$).

In certain embodiments, the system enables one or more physiological parameters to be sensed or measured continuously. In certain embodiments, the system enables one or more physiological parameters to be sensed or measured in real time. In certain embodiments, system enables one or more physiological parameters to be sensed or measured at periodic intervals throughout the ventilation method.

In certain embodiments, the physiological parameter is temperature, pressure, oxygen saturation, pH, heart rate, Doppler signals, electromagnetic fluctuations, or chemical composition. For example, a ventilation system includes or incorporates electrochemical biosensors, or biological micro-electromechanical systems (Bio-MEMS), allowing lab-on-chip (LOC) and incorporation of Micro Total Analysis Systems (µTAS) analysis of biochemical composition of the physiological environment.

In certain embodiments, the physiological parameter is pressure. In certain embodiments, pressure is measured directly via a pressure transducer. For example, in certain embodiments, esophageal pressure is measured directly via an esophageal pressure transducer. In certain embodiments, a pressure transducer is inserted into the patient's esophagus. In certain embodiments, the pressure transducer is in communication with the processor of the system to provide information related to esophageal pressure. Direct measurement of esophageal pressure allows for an estimate of transpulmonary or intrapleural pressure to provide guidance in determining an appropriate ventilation strategy for a patient.

In certain embodiments, one or more esophageal pressure transducers are provided with an esophageal heat transfer device as described in U.S. Pat. Nos. 8,231,664 and 8,444,684 and US Patent Application Publication Nos. 2011/0125234, 2011/0125053, 2012/0265172, and 2013/0006336, the contents of which are hereby incorporated by reference in their entireties. In certain embodiments, one or more pressure transducers are located at any point along a portion of an esophageal heat transfer device intended to be placed within the esophagus. For example, in certain embodiments, one or more pressure transducers are located on the proximal portion of an esophageal heat transfer device to allow measurement of esophageal pressure.

In certain embodiments, one or more pressure transducers are positioned on or within an esophageal heat transfer device. The esophageal heat transfer device includes an inflow lumen connected to a heat transfer medium input port; a heat transfer region; an outflow lumen connected to a heat transfer medium output port; and a distal end configured for insertion into a nostril or mouth of a patient. In certain embodiments, the esophageal heat transfer device is capable of receiving a separate gastric tube or gastric probe. In certain embodiments, the esophageal heat transfer device includes a gastric access tube capable of receiving the separate gastric tube or gastric probe. In certain embodiments, the esophageal heat transfer device includes located at any point along a portion of the esophageal heat transfer device. For example, in certain embodiments, one or more pressure transducers are located on the proximal portion of an esophageal heat transfer device to allow measurement of esophageal pressure.

In certain embodiments, the system enables an operator to set a criterion for the measured physiological parameter. In certain embodiments, the criterion is a target range. In certain embodiments, the criterion is a target value. For example, the system enables an operator to set a pressure criterion for esophageal pressure. In certain embodiments, the criterion for esophageal pressure includes a range or value that is less than 35 cm $H_2O$; alternatively, less than 30 cm $H_2O$; alternatively, less than 25 cm $H_2O$; alternatively, less than 20 cm $H_2O$; alternatively, less than 10 cm $H_2O$. In certain embodiments, the criterion for esophageal pressure includes a range or value that is between 0 and about 25 cm $H_2O$. In certain embodiments, the criterion for esophageal pressure includes a range or value that is between about 5 and about 20 cm $H_2O$. In certain embodiments, the criterion for esophageal pressure includes a range or value that is between 0 and about 10 cm $H_2O$, including values of about 1, about 2, about 3, about 4, about 5, about 6, about 7, about 8, and about 9 cm $H_2O$.

In certain embodiments, the criterion is a target pressure, such as a target esophageal pressure. In certain embodiments, the target pressure is a threshold value. In certain embodiments, the target pressure is a range. In certain embodiments, the target pressure includes an upper and/or a lower limit. In some embodiments, the target pressure is based on a target pleural pressure. For example, in certain embodiments, a target esophageal pressure is determined with reference to a target pleural pressure and/or additional factors, such as patient weight and/or the position of the patient.

In certain embodiments, the system compares the measured physiological parameter to the criterion to determine whether the criterion is satisfied. For example, if the criterion is a threshold value, the system compares the measured physiological parameter to the threshold value to determine whether the measured physiological parameter exceeds or falls below the threshold value. As another example, if the criterion is a range, the system compares the measured physiological parameter to the range to determine whether the measured physiological parameter falls within or outside the range.

In certain embodiments, the ventilation system includes a memory device with a plurality of instructions that will automatically adjust one or more correction factors if a triggering event occurs. For example, in certain embodiments, a triggering event is a measured physiological parameter falling outside of a target range. As another example, a triggering event is a measured physiological parameter departing from a target value. In certain embodiments, the triggering event occurs based on a measured physiological parameter exceeding a threshold value.

In certain embodiments, the ventilation system determines whether a triggering event has occurred. If the ventilation system determines that the triggering event occurred, the ventilation system adjusts one or more correction factors. In certain embodiments, the ventilation system adjusts the correction factor by a default rate, such as 5%, 10%, or 20%. For example, if the ventilation system determines that measured esophageal pressure exceeds target esophageal pressure, the ventilation system reduces a $V_T$ correction factor by 5%. In certain embodiments, the default rate is determined by the degree or magnitude of divergence of the measured physiological parameter from the target range or target value. For example, if the ventilation system determines that measured esophageal pressure exceeds target esophageal pressure by 7%, the ventilation system correspondingly reduces $V_T$ correction factor by 7%.

Alternatively, if the ventilation system determines that the triggering event occurred, the ventilation system adjusts one or more ventilator parameter settings. In certain embodiments, the ventilation system adjusts the ventilator parameter setting by a default rate, such as 5%, 10%, or 20%. For example, if the ventilation system determines that measured esophageal pressure exceeds target esophageal pressure, the ventilation system reduces $V_T$ by 5%. In certain embodiments, the default rate is determined by the degree or magnitude of divergence of the measured physiological parameter from the target range or target value. For example, if the ventilation system determines that measured esophageal pressure exceeds target esophageal pressure by 7%, the ventilation system correspondingly reduces $V_T$ by 7%.

If the ventilation system determines that a triggering event has not occurred, the ventilation system delivers a subsequent breath or series of breaths in a random pattern.

In certain embodiments, the ventilation system randomly delivers a breath or series of breaths. For example, in certain embodiments, the ventilation system employs a predetermined or finite set or pool of breaths or series of breaths. In certain embodiments, each breath or series of breaths is assigned probability data. In one embodiment, each breath or series of breaths is associated with a probability and the ventilation system generates the breath or series of breaths to be provided to the patient based on the associated probabilities. As another example, a random determination is provided through utilization of a random number generator (RNG), such as a true random number generator, a pseudo random number generator, or other suitable randomization process. In these embodiments, since the ventilation system generates a breath or series of breaths randomly or based upon one or more probability calculations, there is no certainty that the ventilation system will ever provide the player with any specific breathing pattern.

In certain embodiments, the ventilation system employs a predetermined or finite set or pool of breaths or series of breaths. In some embodiments, as each breath is provided to the patient, the ventilation system flags or removes the provided breath from the predetermined set or pool. Once flagged or removed from the set or pool, the specific provided breath from that specific pool cannot be provided to the patient again during a predetermined time period. This type of ventilation system provides patients with all of the available breaths over the course of the cycle and guarantees the cumulative volume and pressure over the cycle.

The pool of breaths or series of breaths includes a variety of volumes, pressures, flow rates, and/or frequencies. For example, in certain embodiments, the pool includes breaths along a continuum of volumes, from low tidal volume breaths to high tidal volume breaths, such as "sigh" breaths. In certain embodiments, the pool includes a continuum of pressures and/or flow rates. In certain embodiments, the pool includes a continuum of frequencies between breaths.

In certain embodiments, each breath or series of breaths delivered by the ventilation system has a unique volume, pressure, flow rate, and/or frequency relative to other breaths or series of breaths delivered by the ventilation system. For example, in certain embodiments each breath or series of breaths varies along a continuum of volumes, from low tidal volume breaths to high tidal volume breaths, such as "sigh" breaths. In certain embodiments, each breath or series of breaths varies along a continuum of pressures and/or flow rates. In certain embodiments, the time between each breath delivered by the ventilation system varies along a continuum of frequencies.

In certain embodiments, the ventilation system delivers a subsequent breath or series of breaths based on one or more ventilator parameter settings, one or more correction factors, and a random value. In certain embodiments, the random value is applied to the ventilator parameter setting or the correction factor to obtain a randomized ventilator parameter setting. In certain embodiments, the ventilation system includes a program that will automatically generate a random value. In certain embodiments, the random value is bound by an upper and lower limit. For example, in certain embodiments, the random value is any number between 0 and about 1.5, including about 0.1, about 0.2, about 0.3, about 0.4, about 0.5, about 0.6, about 0.7, about 0.8, about 0.9, about 1.0, about 1.1, about 1.2, about 1.3, and about 1.4. In certain embodiments, the random value is a number between about 0.20 and about 1.25, including about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1.00, about 1.05, about 1.10, about 1.15, and about 1.20.

In certain embodiments, limitations are placed on the number of times that the random value exceeds 1 within a given time period. For example, in certain embodiments, the random number exceeds 1 no more than once a minute, no more than twice a minute, or no more than once every two minutes. As another example, the random number exceeds 1 no more than once every 10 breaths, no more than once every 20 breaths, or no more than once every 40 breaths.

Conversely, in certain embodiments, requirements are placed on the number of times that the random value exceeds 1 within a given time period. For example, in certain embodiments, the random number exceeds 1 at least once a minute, at least twice a minute, or at least once every two minutes. As another example, the random number exceeds 1 at least once every 10 breaths, at least once every 20 breaths, or at least once every 40 breaths. As yet another example, the random number exceeds 1 exactly once a minute, exactly twice a minute, or exactly once every two minutes. As another example, the random number exceeds 1 exactly once every 10 breaths, exactly once every 20 breaths, or exactly once every 40 breaths.

In certain embodiments, a processor applies the random value to one or more ventilator parameter settings or one or more correction factors to obtain a randomized ventilator parameter setting. For example, a processor calculates a randomized ventilator parameter setting based on the ventilator parameter setting set by an operator, a correction factor set by an operator, and/or a correction-factor-adjusted ventilator parameter setting.

For example, the system enables an operator to set $V_T$ to 500 cc, the correction factor to 1, and a target range for esophageal pressure of less than 25 cm $H_2O$. In certain embodiments, the ventilation system delivers a breath or series of breaths at a volume of 500 cc. In certain embodiments, if the measured esophageal pressure is determined to be greater than 25 cm $H_2O$, the correction factor is reduced by, for example, 5% to 0.95. The adjusted correction factor then is applied to $V_T$ to obtain a correction-factor-adjusted $V_T$. In certain embodiments, the ventilation system then delivers a subsequent breath or series of breaths based on the correction-factor-adjusted $V_T$ (i.e., at a volume of 475 cc). Following delivery of a breath or series of breaths at a volume of 475 cc, if the measured esophageal pressure remains greater than 25 cm $H_2O$, the correction factor is again reduced by, for example, 5% to 0.90. Alternatively, if the measured esophageal pressure falls below 25 cm $H_2O$ following delivery of a breath or series of breaths at a volume of 475 cc, the ventilation system applies a random value to the correction-factor-adjusted $V_T$ to obtain a randomized $V_T$. The ventilation system then delivers subsequent breaths or series of breaths based on the randomized $V_T$. As an example, if the processor generates a random value of 0.5, the randomized $V_T$ is 237.5 cc (i.e., 475 cc*0.5).

It should be appreciated that any suitable algorithm may be employed by the ventilation system to adjust and/or randomize the ventilator settings. In certain embodiments, the algorithm may weight any suitable information more or less heavily and consider any suitable information.

The present technology relates a system for providing mechanical ventilation. In certain embodiments, the system includes a patient circuit that includes a tube, a processor, a memory, an operator interface, a flow regulator, and an input device.

In certain embodiments, the ventilation system is capable of delivering a volume of breathing gases to a patient in need thereof. In certain embodiments, the breathing gases are delivered to the patient via a tubing system, such as a one- or two-limb circuit. In certain embodiments, the tubing system is coupled to a patient interface device. In certain embodiments, patient interface devices are invasive or non-invasive and include, but are not limited to, a mouthpiece, a nasal mask, nasal pillows, a full face mask (oronasal mask), an endotracheal tube, a laryngeal mask, and a tracheostomy tube.

In certain embodiments, the ventilation system also includes a processor and a flow regulator. The flow regulator regulates the flow of breathing gases to the patient. The flow regulator includes a drive mechanism and/or one or more flow control valves, such as a proportional solenoid valve. In certain embodiments, the operation of the flow regulator is controlled by the processor.

In certain embodiments, the ventilation system also includes an operator interface. The operator interface is communicably connected to the processor such that the processor is capable of receiving operator input. Such operator input includes manipulating one or more ventilator settings, such as mode of ventilation, tidal volume, respiratory rate, inspiratory flow rate, inspiratory-to-expiratory time ratio, and/or positive end expiratory pressure. In certain embodiments, operator input includes establishing criteria, such as a range or threshold value, for a measured physiological parameter. For example, in certain embodiments, the physiological parameter is pressure, such as transpleural or esophageal pressure; temperature; functional residual capacity; and/or blood gas levels.

In certain embodiments, the operator interface includes, for example, a control panel and/or a display device. The control panel includes one or more knobs or buttons that enable the operator to manipulate certain settings of the ventilation system. In certain embodiments, the display device presents certain images and/or information to the use. For example, in certain embodiments, the display device provides clinical data and/or alerts to the health care provider.

It should be appreciated that, in certain embodiments, the ventilation system of the present disclosure is configured to enable users to employ an operator interface to access the processor through the Internet or any other suitable data network, such as a mobile communications network, a local area network (LAN), or a wide area network (WAN). For example, in certain embodiments, the ventilation system includes a remote operator interface that enables an operator to provide input or view output from a remote location.

In certain embodiments, the ventilation system also includes an input device to detect the physiological parameter or receive information about a physiological parameter. The input device is communicably connected to the processor such that the processor is capable of receiving input from the input device. For example, in certain embodiments, the input device is a pressure transducer, a thermometer, an imaging device, a carbon dioxide monitor, or an oxygen monitor. In certain embodiments, the imaging device is an electrical impedance tomography (EIT) device. Alternatively, the input device includes an operator interface that allows an operator to input information about a physiological parameter. In certain embodiments, the pressure transducer is an esophageal pressure transducer.

In certain embodiments, the ventilation system is configured to provide mechanical ventilation as described herein. For example, in certain embodiments, the ventilation system is capable of receiving one or more settings for one or more ventilator parameters. In certain embodiments, the ventilation system is capable of receiving one or more criterion for one or more physiological parameters, such as pressure. In certain embodiments, the ventilation system is capable of delivering a breath or a series of breaths based on the ventilator parameters. In certain embodiments, the ventilation system is capable of measuring the physiological parameter after the breath or a series of breaths has been delivered. In certain embodiments, the ventilation system is capable of determining whether the measured physiological parameter satisfies the criterion. In certain embodiments, the ventilation system is capable of: (i) delivering a subsequent breath or series of breaths based on the ventilator parameters adjusted by a random value and/or (ii) adjusting one or more of the ventilator parameters by a default amount and delivering a subsequent breath or series of breaths based on the adjusted ventilator parameters. In certain embodiments, the ventilation system is capable of receiving one or more settings for one or more ventilator parameters; receiving one or more criterion for one or more physiological parameters, such as pressure; delivering a breath or a series of breaths based on the ventilator parameters; measuring the physiological parameter after the breath or a series of breaths has been delivered; determining whether the measured physiological parameter satisfies the criterion; and, (i) if the measured physiological parameter satisfies the criterion, delivering a subsequent breath or series of breaths based on the ventilator parameters adjusted by a random value, or (ii) if the measured physiological parameter does not satisfy the criterion, adjusting one or more of the ventilator parameters by a default amount and delivering a subsequent breath or series of breaths based on the adjusted ventilator parameters.

In certain embodiments, the ventilation system is configured to provide mechanical ventilation as described herein. For example, in certain embodiments, the ventilation system is capable of receiving one or more settings for one or more ventilator parameters. In certain embodiments, the ventilation system is capable of receiving one or more correction factors. In certain embodiments, the ventilation system is capable of receiving one or more criterion for one or more physiological parameters, such as pressure. In certain embodiments, the ventilation system is capable of delivering a breath or a series of breaths based on the ventilator parameters and the correction factor(s). In certain embodiments, the ventilation system is capable of measuring the physiological parameter after the breath or a series of breaths has been delivered. In certain embodiments, the ventilation system is capable of determining whether the measured physiological parameter satisfies the criterion. In certain embodiments, the ventilation system is capable of delivering a subsequent breath or series of breaths based on (i) the ventilator parameters and the correction factor(s), further adjusted by a random value and/or (ii) adjusting the correction factor by a default amount and delivering a subsequent breath or series of breaths based on the ventilator parameters and the adjusted correction factor. In certain embodiments, the ventilation system is capable of receiving one or more settings for one or more ventilator parameters; receiving one or more correction factors; receiving one or more criterion for one or more physiological parameters, such as pressure; delivering a breath or a series of breaths based on the ventilator parameters and the correction factor (s); measuring the physiological parameter after the breath or a series of breaths has been delivered; determining whether the measured physiological parameter satisfies the criterion; and, (i) if the measured physiological parameter satisfies the criterion, delivering a subsequent breath or series of breaths based on the ventilator parameters and the correction factor(s), further adjusted by a random value, or (ii) if the measured physiological parameter does not satisfy the criterion, adjusting the correction factor by a default amount and delivering a subsequent breath or series of breaths based on the ventilator parameters and the adjusted correction factor.

The present technology relates to a method and system for providing passive ventilation via an invasive artificial airway, such as an endotracheal tube or tracheostomy tube. In certain embodiments, the method or system provides continuous, passive ventilation through an endotracheal tube or tracheostomy tube of an invasively ventilated patient.

In certain embodiments, a ventilation system is capable of providing continuous, passive ventilation through an endotracheal tube or tracheostomy tube of an invasively ventilated patient.

In certain embodiments, the ventilation system is configured to provide continuous, passive ventilation as described herein. For example, in certain embodiments, the ventilation system is capable of receiving operator input via an operator interface. In certain embodiments, the ventilation system is capable of delivering a continuous flow of breathing gas based on the operator input. In certain embodiments, a ventilation system includes a processor capable of providing signals to a flow regulator such that the flow regulator regulates the flow of breathing gas to an invasively ventilated patient. In certain embodiments, the flow is continuous. In certain embodiments, the flow is passive.

Certain example embodiments of the presently described technology now will be described with respect to the appended figures; however, the scope of the present technology is not intended to be limited thereby. It is to be understood that the scope of the present technology is not to be limited to the specific embodiments described herein. The technology may be practiced other than as particularly described and still be within the scope of the claims.

FIG. 1 shows a flow diagram of a method 100 for operating a ventilation system in accordance with a specific embodiment of the present technology. According to various embodiments, at least a portion of the activity described with respect to FIG. 1 may be implemented via one or more ventilation systems described herein.

As shown at 102, a ventilation system enables an operator (e.g., a healthcare provider or caregiver) to set or select an initial setting for one or more ventilator parameters. In certain embodiments, ventilator parameters include the mode of operation of the ventilator and/or volume, pressure, and/or flow parameters such as $V_T$, PEEP, $FiO_2$, and/or respiratory rate. In certain embodiments, the ventilator parameter is $V_T$. For example, in certain embodiments, an operator employs an operator interface of a ventilation system to select a volume of 500 cc for $V_T$. During the ventilation method, the setting may be adjusted manually or automatically, as further described herein.

The ventilation system enables an operator to set or select a target esophageal pressure ($P_{targ}$), as indicated by block 104. In certain embodiments, the target pressure is a threshold value or a range. The target pressure includes an upper and/or a lower limit. In certain embodiments, the target esophageal pressure is between 0 and about 35 cm $H_2O$. For example, in certain embodiments, an operator employs an operator interface of a ventilation system to set a $P_{targ}$ of less than 25 cm $H_2O$.

The ventilation system delivers a volume of gas based on the ventilator parameter settings, as indicated by block 106. In one embodiment, the volume of gas is a breath or a series of breaths. In the first iteration, the current ventilator parameter setting will be the ventilator parameter setting set in block 102. In subsequent iterations, the current ventilator parameter setting is an adjusted ventilator parameter setting as described herein.

In certain embodiments, the ventilation system provides signals to a flow regulator based on operator input, such as a setting for one or more ventilator parameters. The flow regulator includes one or more drive mechanisms and/or one or more valves that respond to signals from the processor to regulate the flow of breathing gas to the patient.

Esophageal pressure ($P_{Eso}$) is measured, as indicated by block 108. In certain embodiments, esophageal pressure is measured via esophageal manometry. In certain embodiments, a balloon is placed in the patient's esophagus to measure esophageal pressure. In certain embodiments, the ventilation system measures the esophageal pressure through a pressure transducer placed in the patient's esophagus. In certain embodiments, the ventilation system continuously measures the esophageal pressure. In certain embodiments, the ventilation system measures the esophageal pressure after each breath or series of breaths.

As indicated by decision diamond 110, the ventilation system compares target esophageal pressure to measured esophageal pressure. In certain embodiments, the measured esophageal pressure is a single measurement taken after a breath or series of breaths has been delivered by the ventilation system. In certain embodiments, the ventilation system compares a mean measured esophageal pressure to the target esophageal pressure.

If measured esophageal pressure differs from target esophageal pressure, then the ventilation system adjusts the setting for the one or more ventilator parameters as indicated by block 112. In certain embodiments, the ventilation system adjusts the ventilator parameter setting by a predetermined amount or, in a series of iterations, at a default rate. For example, in certain embodiments, the ventilation system reduces the ventilator parameter setting by 5% in each iteration through mechanical ventilation method 100. In certain embodiments, the ventilation system adjusts the ventilator parameter setting based on the measured esophageal pressure. For example, in certain embodiments, the adjustment to the ventilator parameter setting or the new ventilator parameter setting is determined based on the magnitude by which measured esophageal pressure differs from target esophageal pressure. Following adjustment of the one or more ventilator parameters, the ventilation system delivers a breath or a series of breaths based on the current ventilator parameter settings, as shown in block 106.

If measured esophageal pressure does not differ from target esophageal pressure, then the ventilation system delivers a breath or series of breaths based on the current ventilator parameter settings and a random value, as indicated by block 114. In certain embodiments, the random value is 0 or 1 or any real number between 0 and 1. In certain embodiments, the random value is generated by the processor. In certain embodiments, the random value is applied to the ventilator parameter settings to determine a randomized ventilator parameter.

Figure 2:
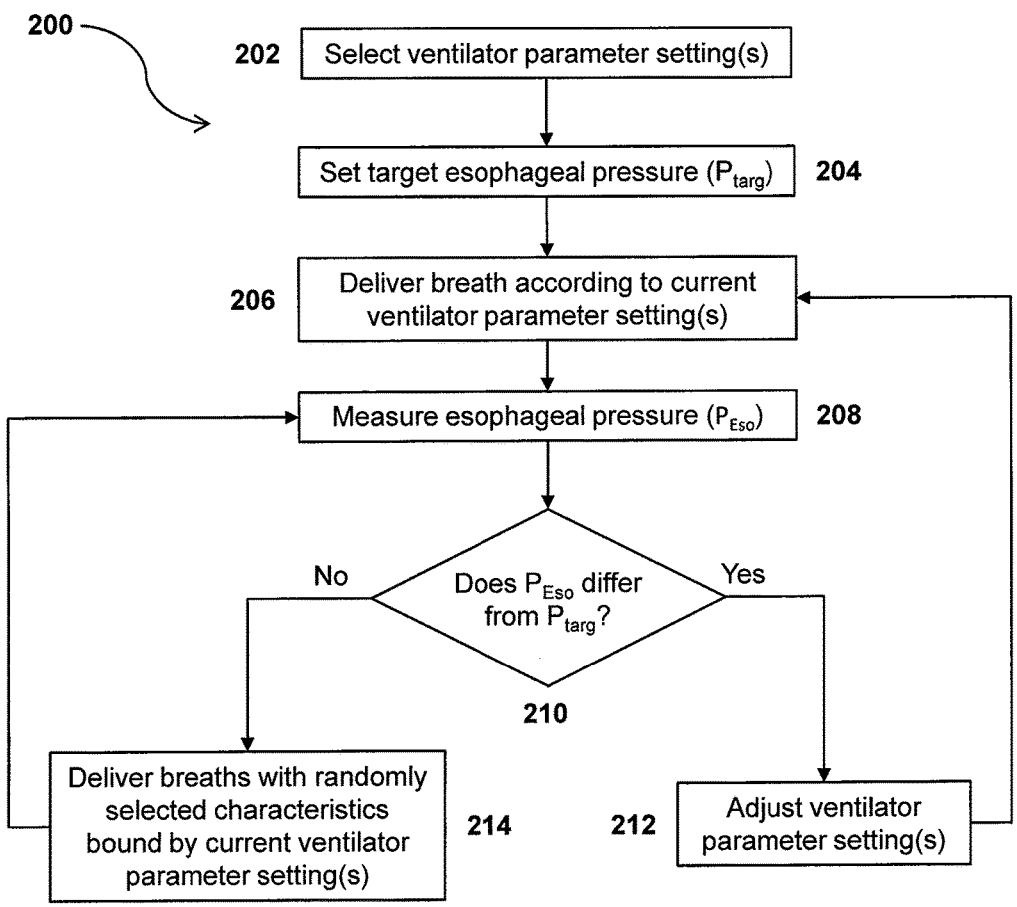
FIG. 2 shows a flowchart of another embodiment of the present technology.

FIG. 2 shows a flow diagram of a method 200 for operating a ventilation system in accordance with a specific embodiment of the present technology. According to various embodiments, at least a portion of the activity described with respect to FIG. 2 may be implemented via one or more ventilation systems described herein.

Steps depicted in blocks 202-212 may be carried out in accordance with the corresponding blocks of FIG. 1.

As shown in decision diamond 210, the ventilation system compares the target esophageal pressure and measured esophageal pressure.

If measured esophageal pressure does not differ from target esophageal pressure, then the ventilation system delivers a breath or series of breaths with randomly selected characteristics. The characteristics include, but are not limited to, volume, pressure, flow rate, and frequency. In certain embodiments, one or more of the characteristics is a fixed value. For example, in certain embodiments, the frequency of breaths delivered in mechanical ventilation method 200 is fixed at a rate of 12 bpm. In certain embodiments, at least one of the characteristics varies for each breath or series of breaths provided by the ventilation system. For example, in certain embodiments, each breath or series of breaths varies along a continuum of volumes, from low tidal volume breaths to high tidal volume breaths, such as "sigh" breaths. In certain embodiments, the ventilation system employs a predetermined or finite set or pool of breaths or series of breaths as described herein.

Figure 3:
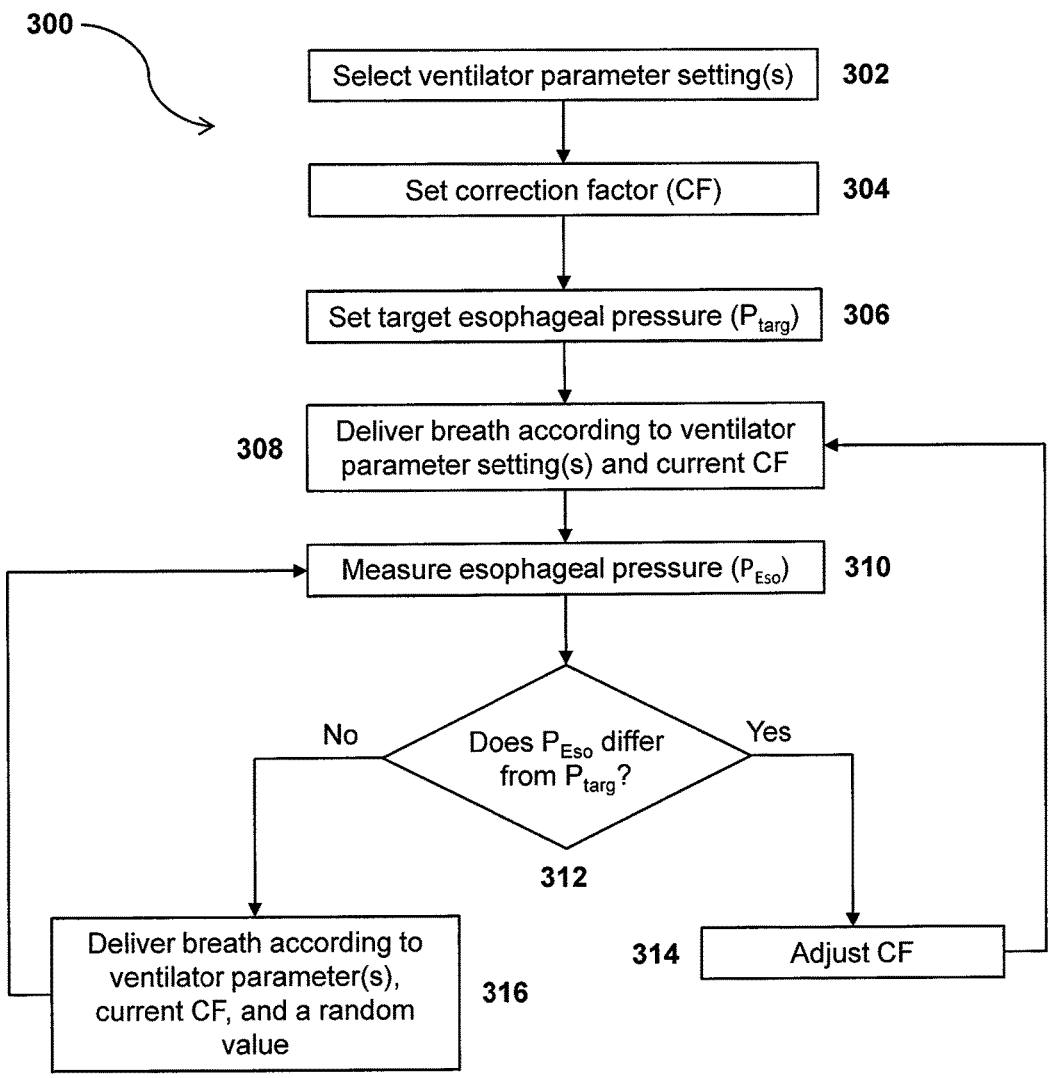
FIG. 3 shows a flowchart of another embodiment of the present technology.

FIG. 3 shows a flow diagram of a method 300 for operating a ventilation system in accordance with a specific embodiment of the present technology. According to various embodiments, at least a portion of the activity described with respect to FIG. 3 may be implemented via one or more ventilation systems described herein.

The ventilation system enables an operator (e.g., a healthcare provider or caregiver) to set or select an initial setting for one or more ventilator parameters, as indicated by block 302. In certain embodiments, ventilator parameters include volume, pressure, and/or flow parameters such as $V_T$, PEEP, $FiO_2$, and/or respiratory rate. In certain embodiments, the ventilator parameter is $V_T$. For example, in certain embodiments, an operator employs an operator interface of a ventilation system to select a volume of 500 cc for $V_T$.

The ventilation system enables an operator to set or select a correction factor for at least one of the one or more ventilator parameters, as indicated by block 304. In certain embodiments, the correction factor is any real number and, in particular, a number between about 0 and about 1.50. In certain embodiments, the correction factor is 1. For example, in certain embodiments, an operator employs an operator interface of a ventilation system to set the correction factor for $V_T$ to 1. In certain embodiments, prior to delivering a volume of gas to a patient, the ventilation system applies the correction factor to the setting for the ventilation parameter to obtain a correction-factor-adjusted setting. For example, if an operator selected a volume of 500 cc for $V_T$ and a correction factor of 0.80, in certain embodiments, the ventilation system calculates a correction-factor-adjusted setting of 400 cc for $V_T$. During ventilation, the correction factor may be adjusted manually or automatically, as further described herein.

The ventilation system also enables an operator to set or select a target esophageal pressure ($P_{targ}$), as indicated by block 306. In certain embodiments, the target pressure is a threshold value or a range. The target pressure includes an upper and/or a lower limit. In certain embodiments, the target esophageal pressure is between 0 and about 35 cm $H_2O$. For example, in certain embodiments, an operator employs an operator interface of a ventilation system to set a $P_{targ}$ of less than 25 cm $H_2O$.

The ventilation system delivers a volume of gas (e.g., a breath or a series of breaths) based on the ventilator settings and the current correction factor(s), as indicated by block 308. In the first iteration, the current correction factor will be the correction factor set in block 304. In subsequent iterations, the current correction factor is an adjusted correction factor as described herein.

In certain embodiments, the ventilation system receives and integrates operator input, such as a setting for one or more ventilator parameters and a correction factor. In certain embodiments, the ventilation system then provides signals to a flow regulator. The flow regulator includes one or more drive mechanisms and/or one or more valves that respond to signals from the processor to regulate the flow of breathing gas to the patient.

The ventilation system measures the esophageal pressure ($P_{Eso}$), as indicated by block 310. In certain embodiments, the ventilation system measures the esophageal pressure via esophageal manometry. In certain embodiments, the ventilation system measures the esophageal pressure via a balloon placed in the patient's esophagus. In certain embodiments, the ventilation system measures the esophageal pressure through a pressure transducer placed in the patient's esophagus. In certain embodiments, the ventilation system continuously measures the esophageal pressure. In certain embodiments, the ventilation system measures the esophageal pressure after each breath or series of breaths.

As indicated by decision diamond 312, the processor of the ventilation system compares target esophageal pressure to measured esophageal pressure. In certain embodiments, the measured esophageal pressure is a single measurement taken after a breath or series of breaths has been delivered by the ventilation system. In certain embodiments, the ventilation system compares a mean measured esophageal pressure to the target esophageal pressure.

If measured esophageal pressure differs from target esophageal pressure, then the correction factor is adjusted as indicated by block 314. In certain embodiments, the ventilation system adjusts the correction factor by a predetermined amount or, in a series of iterations, at a default rate. For example, in certain embodiments, the ventilation system reduces the correction factor by 5% in each iteration through mechanical ventilation method 300. In certain embodiments, the ventilation system adjusts the correction factor based on the measured esophageal pressure. For example, in certain embodiments, the adjustment to the correction factor or the new correction factor is determined based on the magnitude by which measured esophageal pressure differs from target esophageal pressure. Following adjustment of the correction factor, the ventilation system delivers a breath or a series of breaths based on the ventilator settings and the current correction factor(s), as shown in block 308.

If measured esophageal pressure does not differ from target esophageal pressure, then the ventilation system delivers a breath or series of breaths based on the ventilator settings, the current correction factor, and a random value as indicated by block 316. In certain embodiments, the random value is generated by the processor. In certain embodiments, the random value is applied to the ventilator settings and/or the current correction factor to determine a randomized ventilator parameter.

Figure 4:
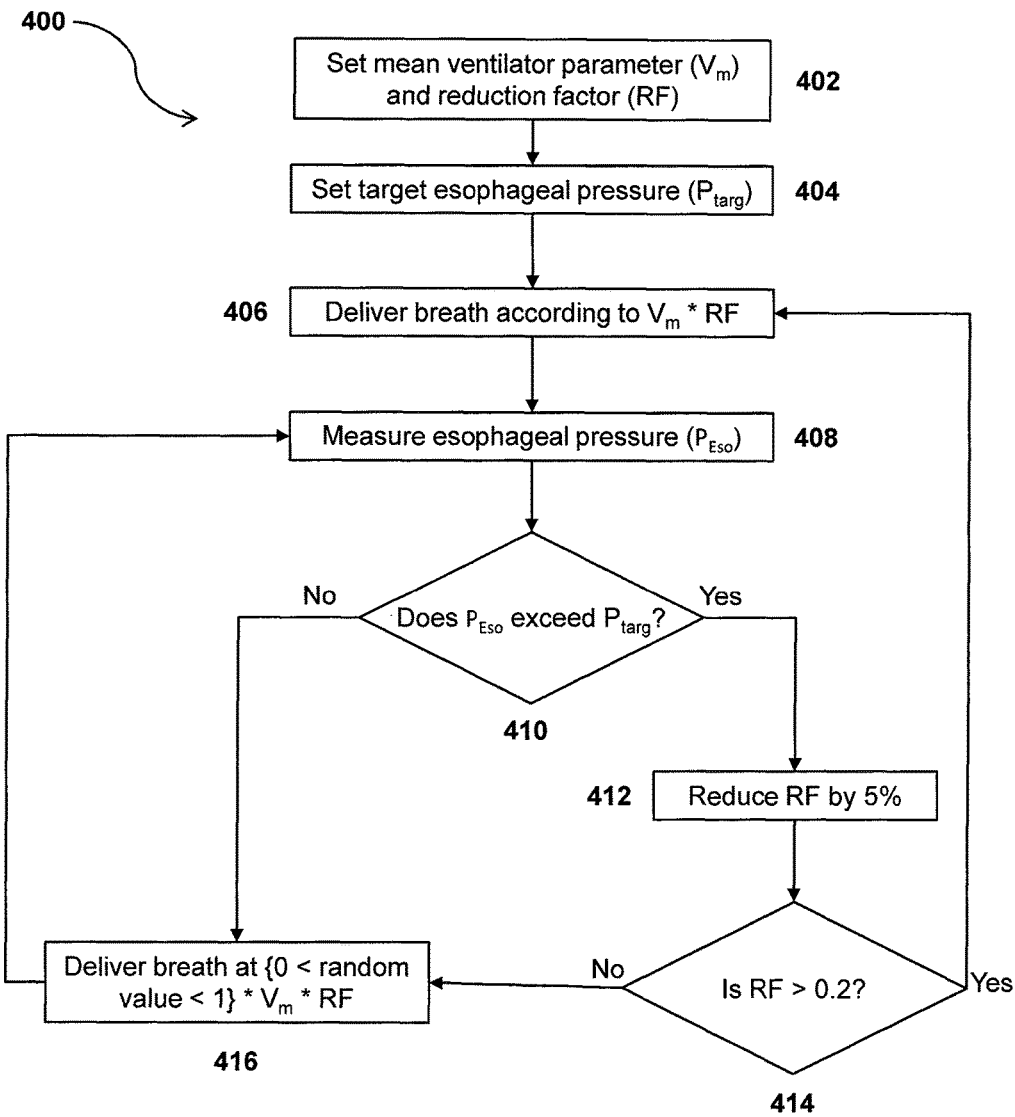
FIG. 4 shows a flowchart of another embodiment of the present technology.

FIG. 4 shows a flow diagram of a method 400 for operating a ventilation system in accordance with a specific embodiment of the present technology. According to various embodiments, at least a portion of the activity described with respect to FIG. 4 may be implemented via one or more ventilation systems described herein.

A ventilation system enables an operator (e.g., a healthcare provider or caregiver) to set or select a mean ventilator parameter and a reduction factor, as indicated by block 402. In certain embodiments, the mean ventilator parameter includes mean tidal volume ($V_m$). For example, in certain embodiments, an operator employs an operator interface of a ventilation system to select a mean tidal volume of 500 cc. In certain embodiments, the reduction factor is any real number and, in particular, a number between about 0.20 and about 1.50. In certain embodiments, the reduction factor is 1. For example, in certain embodiments, an operator employs an operator interface of a ventilation system to set the reduction factor for $V_m$ to 1. In certain embodiments, prior to delivering a volume of gas to a patient, a processor of a ventilation system applies the reduction factor to the mean ventilator parameter to obtain a reduction-factor-adjusted parameter. For example, if an operator selected a volume of 500 cc for $V_m$ and a reduction factor of 0.80, in certain embodiments, the ventilation system calculates a reduction-factor-adjusted parameter of 400 cc for $V_m$. During the ventilation method, the reduction factor may be adjusted manually or automatically, as further described herein.

The ventilation system enables an operator to set or select a target esophageal pressure ($P_{targ}$), as indicated by block 404. In certain embodiments, the target pressure is a threshold value or a range. In certain embodiments, the target pressure includes an upper and/or a lower limit. In certain embodiments, the target esophageal pressure includes values or ranges between 0 and about 35 cm $H_2O$. For example, in certain embodiments, an operator employs an operator interface of a ventilation system to set a $P_{targ}$ of less than 25 cm $H_2O$.

The ventilation system delivers a breath or a series of breaths based on the mean ventilator parameter and the current reduction factor(s), as indicated by block 406. In the first iteration, the current reduction factor will be the reduction factor set in block 402. In subsequent iterations, the current reduction factor is an adjusted reduction factor as described herein.

In certain embodiments, the ventilation system receives and integrates operator input, such as a mean ventilator parameter and a reduction factor. In certain embodiments, the ventilation system then provides signals to a flow regulator. The flow regulator includes one or more drive mechanisms and/or one or more valves that respond to signals from the processor to regulate the flow of breathing gas to the patient.

Esophageal pressure ($P_{Eso}$) is measured as previously described herein, as indicated by block 408.

As indicated by decision diamond 410, the ventilation system compares target esophageal pressure to measured esophageal pressure. In certain embodiments, the measured esophageal pressure is a single measurement taken after a breath or series of breaths has been delivered by the ventilation system. In certain embodiments, the ventilation system compares a mean measured esophageal pressure to the target esophageal pressure If measured esophageal pressure exceeds target esophageal pressure, then the reduction factor is reduced by 5% to obtain an adjusted reduction factor as indicated by block 412. If the adjusted reduction factor is greater than 0.2, the ventilation system delivers a breath or a series of breaths based on the mean ventilator parameter and the current reduction factor(s), as shown in step 406. If the adjusted reduction factor is less than 0.2, then the ventilator delivers a breath or series of breaths based on the mean ventilator parameter, the current reduction factor, and a random value as indicated by block 416.

Likewise, if measured esophageal pressure does not exceed target esophageal pressure, then the ventilator delivers a breath or series of breaths based on the mean ventilator parameter, the current reduction factor, and a random value as indicated by block 416.

In certain embodiments, the random value is 0 or 1 or any real number between 0 and 1. In certain embodiments, the random value is generated by the processor. In certain embodiments, the random value is applied to the ventilator parameter settings to determine a randomized ventilator parameter.

Figure 5:
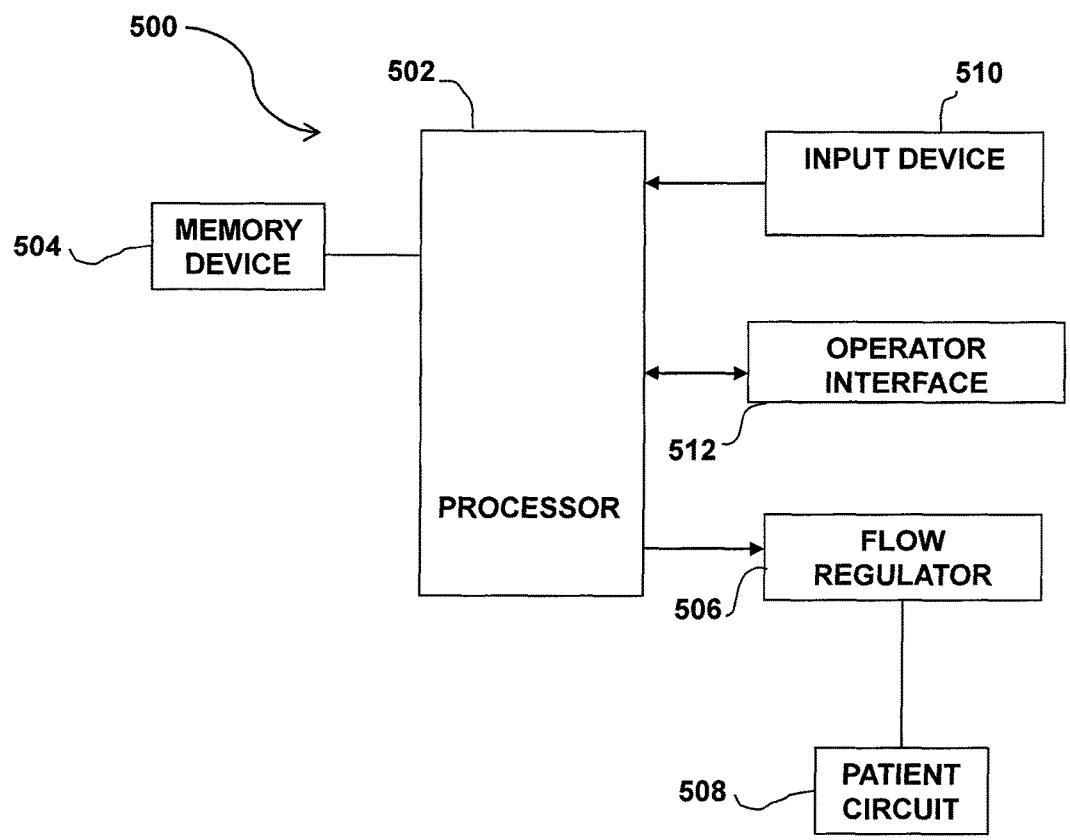
FIG. 5 shows a block diagram illustrating components of a ventilation system that may be used for implementing various aspects of example embodiments.

FIG. 5 is a diagram illustrating an embodiment of a ventilation system 500 of the present technology. The ventilation system 500 includes at least one processor 502, at least one memory device 504, at least one flow regulator 506, at least one patient circuit 508, at least one input device 510, and at least one operator interface 512.

The ventilation system 500 includes at least one processor 502. The processor 502 is configured to communicate with, configured to access, and configured to exchange signals with at least one memory device 504. The memory device 504 is computer-readable storage media that stores software that is executed by the processor 502 and which controls the operation of at least one flow regulator 506 in order to control the breathing assistance provided to the patient by the ventilation system 500. In various embodiments, the at least one memory device 504 includes random access memory (RAM), which can include non-volatile RAM (NVRAM), magnetic RAM (MRAM), ferroelectric RAM (FeRAM), and other forms as commonly understood in the health care industry. In other embodiments, the at least one memory device 504 includes read only memory (ROM). In certain embodiments, the at least one memory device 504 includes flash memory and/or EEPROM (electrically erasable programmable read only memory). Any other suitable magnetic, optical, and/or semiconductor memory may operate in conjunction with the ventilation system 500 disclosed herein. In certain embodiments, the at least one processor 502 and the at least one memory device 504 both reside within a cabinet of the ventilation system 500. In other embodiments, at least one of the at least one processor 502 and the at least one memory device 504 reside outside the cabinet of the ventilation system 500.

In certain embodiments, as generally described above, the at least one memory device 504 stores program code and instructions executable by the at least one processor 502 to control the ventilation system 500. In certain embodiments, memory device 504 also is configured to store, without limitation, executable instructions, operating systems, applications, resources, installation scripts and/or any other type of data suitable for use with the methods and systems described herein. Instructions for operating systems and applications are located in a functional form on non-transitory memory for execution by processor 502 to perform one or more of the processes described herein. In particular, in certain embodiments, the at least one memory device 504 stores operating data, such as image data, event data, input data, random number generators (RNGs) or pseudo-RNGs, and/or applicable parameters that relate to the function of the ventilation system 500. In various embodiments, part or all of the program code and/or the operating data described above is stored in at least one detachable or removable memory device including, but not limited to, a cartridge, a disk, a CD ROM, a DVD, a USB memory device, or any other suitable non-transitory computer readable medium. In certain such embodiments, such a removable memory device in ventilation system 500 enables an operator (such as, for example, a healthcare provider or caregiver) to implement at least part of the present disclosure. In other embodiments, part or all of the program code and/or the operating data is downloaded to the at least one memory device 504 through any suitable data network, such as an internet or intranet.

Flow regulator 506 regulates delivery of gas from a gas source to a patient according to the ventilator settings prescribed for the patient. For example, in certain embodiments, flow regulator 506 regulates the flow of gas into a ventilatory circuit, such as patient circuit 508, and thereby into a patient's lungs. In certain embodiments, flow regulator 506 is generally configured to process various inputs (e.g., input from operator interface 512, ventilation programs stored in memory device 504, and/or feedback from input device 510) to regulate the flow of gas into a patient. In certain embodiments, flow regulator 506 receives pressurized gas from a compressor or centralized pressurized air source, such as wall outlet in a hospital. In certain embodiments, flow regulator 506 includes a valve, such as a solenoid valve. In certain embodiments, the concentration and pressure of gas delivered to the patient is controlled by valves of flow regulator 506. In certain embodiments, flow regulator 506 generates pressurized gas. In certain embodiments, flow regulator 506 includes a motorized blower or mechanical drive mechanism. In certain embodiments, the concentration and pressure of gas delivered to the patient is controlled by, for example, the motor speed and on/off configuration of the motorized blower or mechanical drive mechanism. In certain embodiments and as described above, the gas source is a component of ventilation system 500. For example, in certain embodiments, the gas source is a bellows, piston, compressor, blower, or the like. In certain embodiments, the gas source is independent of ventilation system 500. For example, in certain embodiments, the gas source is a wall supply in a hospital or a storage tank, such as a pressurized oxygen storage tank.

The ventilation system 500 includes a patient circuit 508 for circulating the inspiratory gas and the expiratory gas between the flow regulator 506 and a patient (not shown). The ventilation system 500 further includes an inspiratory port and an expiratory port through which the inspiratory gas and the expiratory gas are supplied to and received from the patient through the patient circuit 508. In certain embodiments, the patient circuit 508 can be a Y circuit that is used to connect the flow regulator 506 to the patient. The patient circuit 508 includes an inspiratory limb with one end coupled to an inspiratory port and an expiratory limb with one end coupled to an expiratory port of the flow regulator 506. The other ends of the inspiratory limb and the expiratory limb are coupled to a breathing piece that is applied to the patient via, for example, an endotracheal tube or mask (not shown).

The ventilation system 500 includes at least one input device 510 capable of sensing or measuring one or more parameters, such as a physiological parameter. The input device 510 is coupled to processor 502 such that processor 502 receives input, such as data and/or measurements, from input device 510. In certain embodiments, the input device is a sensor associated with the patient or the patient circuit 508. Representative data received from the input device 510 includes, for example, measurements of or data sufficient to calculate inspiratory time ($T_I$); expiratory time ($T_E$); inspiratory flow rate ($F_I$); expiratory flow rate ($F_E$); fraction of inspired oxygen ($FiO_2$); tidal volume ($V_T$); end tidal $CO_2$ ($EtCO_2$); mean airway pressure ($P_{mean}$); peak inspiratory pressure (PIP); continuous airway pressure (CPAP); positive end expiratory pressure (PEEP); transpulmonary pressure ($P_{tp}$); esophageal pressure ($P_{Eso}$); respiratory rate; core body temperature (CBT); arterial blood oxygen saturation levels ($SaO_2$); blood pressure (BP); and pulse rate (PR).

Operator interface 512 enables an operator, such as, for example, a healthcare provider to monitor the operation of and interact with the ventilation system 500. The operator interface 512 is coupled to processor 502. Operator interface 512 includes, for example, a control panel and/or a display device. The control panel includes one or more knobs or buttons that enable the operator (for example, a healthcare provider or caregiver) to control certain settings of ventilation system 500. Based on the input data or information, the processor 502 is operative to control the flow regulator 506 for performing the desired operations. The display device presents various displays, viewable by an operator, for displaying useful clinical data and alerts to the health care provider. The display device is capable of displaying any type of ventilation information, such as sensor readings, parameters, commands, alarms, warnings, and smart prompts (i.e., ventilator determined operator suggestions). In addition, in certain embodiments, the display device is further configured to receive input from an operator. For example, in certain embodiments, the display device is configured as a touch-screen input device. Alternatively, in certain embodiments, the ventilation system 500 enables an operator to interact with ventilation system 500 via another type of operator interface 512, such as by a keyboard or other suitable interactive device.

In certain embodiments, the memory device 504 stores one or more sensor measurements related to patient status. In certain embodiments, a visualization of past patient measurements is displayed on, for example, a display device of operator interface 512. In certain embodiments, the past patient measurements are displayed on a timeline and/or in a graphical or numerical format.

In certain embodiments, a scale representing an airway pressure of the patient is displayed with the past patient measurements. In certain embodiments, alerts are displayed on a display device of operator interface 512. The alerts represent a patient measurement falling outside of a compliance range for that parameter. In certain embodiments, an alert provides immediate access to the display and/or settings window associated with an alert event. For example, in certain embodiments, the system enables an operator to view and/or adjust ventilator settings via an associated alert settings window.

In certain embodiments, the term "patient" refers to a mammal in need of therapy for a condition, disease, or disorder or the symptoms associated therewith. The term "patient" includes dogs, cats, pigs, cows, sheep, goats, horses, rats, mice and humans. The term "patient" does not exclude an individual that is normal in all respects.

In the preceding paragraphs, use of the singular includes the plural except where specifically indicated. As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof.

Certain aspects of the of the present technology in particular pertain to the following:

1. A method of operating a ventilation system, the method comprising:
    (a) causing a processor to execute a plurality of instructions stored in a memory device to operate with a flow regulator to deliver a volume of gas to a lung of a patient according to
        (i) a setting for one or more ventilator parameters and
        (ii) one or more adjustment factors;
    (b) causing the processor to execute the plurality of instructions to operate with an input device to detect whether a physiological parameter exceeds a threshold; and
    (c) causing the processor to execute the plurality of instructions to vary at least one of the adjustment factors, wherein:
        (i) if the physiological parameter exceeds the threshold, at least one of the adjustment factors is reduced at a default rate, and
        (ii) if the physiological parameter does not exceed the threshold, at least one of the adjustment factors is varied randomly.

2. The method of item 1, wherein the flow regulator includes one or more valves.

3. The method of item 1 or 2, wherein the one or more ventilator parameters are selected from the group consisting of: (i) tidal volume; (ii) respiratory rate; (iii) inspiratory flow rate; (iv) inspiratory-to-expiratory time ratio (I:E); and (v) positive end expiratory pressure.

4. The method of any one of items 1 to 3, wherein the input device is a pressure transducer.

5. The method of any one of items 1 to 4, wherein the physiological parameter is esophageal pressure.

6. The method of any one of items 1 to 5, wherein the default rate is about 5%.

7. The method of any one of items 1 to 6, wherein at least one of the adjustment factors is reduced at the default rate until the physiological parameter is determined to be below the threshold.

8. A method of operating a ventilation system, the method comprising:
    (a) causing a processor to execute a plurality of instructions stored in a memory device to operate with a flow regulator to deliver a volume of gas to a lung of a patient according to at least one setting for one or more ventilator parameters;
    (b) causing the processor to execute the plurality of instructions to operate with an operator interface to enable an operator to set the one or more ventilator settings;
    (c) causing the processor to execute the plurality of instructions to operate with the operator interface to enable the operator to set at least one criterion for a physiological parameter;
    (d) causing the processor to execute the plurality of instructions to operate with an input device to detect the physiological parameter;
    (e) causing the processor to execute the plurality of instructions to vary at least one of the settings, wherein:
        (i) if the criterion is satisfied, at least one of the settings is reduced at a default rate, and
        (ii) if the criterion is not satisfied, at least one of the settings is varied randomly.

9. The method of item 8, wherein the flow regulator includes one or more valves.

10. The method of item 8 or 9, wherein the one or more ventilator parameters are selected from the group consisting of: (i) tidal volume; (ii) respiratory rate; (iii) inspiratory flow rate; (iv) inspiratory-to-expiratory time ratio (I:E); and (v) positive end expiratory pressure.

11. The method of any one of items 8 to 10, wherein the input device is a pressure transducer.

12. The method of any one of items 8 to 11, wherein the physiological parameter is esophageal pressure.

13. The method of any one of items 8 to 12, wherein the at least one criterion is esophageal pressure less than about 25 cm $H_2O$.

14. The method of any one of items 8 to 13, wherein the default rate is about 5%.

15. A non-transitory computer readable medium including a plurality of instructions which, when executed by a processor, cause the processor to:
    (a) operate with a flow regulator to deliver a volume of gas to a lung of a patient according to (i) one or more ventilator settings and (ii) one or more adjustment factors;
    (b) operate with an input device to detect whether a physiological parameter exceeds a threshold;
    (c) vary at least one of the adjustment factors, wherein:
        (i) if the physiological parameter exceeds the threshold, at least one of the adjustment factors is reduced at a default rate, and
        (ii) if the physiological parameter does not exceed the threshold, at least one of the adjustment factors is varied randomly.

16. A non-transitory computer readable medium including a plurality of instructions which, when executed by a processor, cause the processor to:
    (a) operate with a flow regulator to deliver a volume of gas to a lung of a patient according to one or more ventilator settings;
    (b) operate with an operator interface to enable an operator to set the one or more ventilator settings;
    (c) operate with the operator interface to enable the operator to set at least one criterion for a physiological parameter;
    (d) operate with an input device to detect the physiological parameter;
    (e) vary at least one of the one or more ventilator settings, wherein:
        (i) if the criterion is satisfied, at least one of the ventilator settings is reduced at a default rate, and (ii) if the criterion is not satisfied, at least one of the ventilator settings is varied randomly.

17. A system for providing ventilation assistance or control, the system comprising:
   (a) at least one processor;
   (b) at least one operator interface configured to provide input to the processor;
   (c) at least one input device; and
   (d) at least one memory device that stores a plurality of instructions, which when executed by the at least one processor, cause the at least one processor to;
      (i) operate with the at least one operator interface to receive a first setting for a ventilator parameter and a criterion for a physiological parameter;
      (ii) cause a first volume of gas to be delivered to a patient in accordance with the first setting;
      (iii) operate with the at least one input device to receive a measured value for the physiological parameter;
      (iv) determine whether the measured value satisfies the criterion; and
      (v) cause a second volume of gas to be delivered to a patient, wherein the second volume of gas is delivered in accordance with
         (1) a randomized setting or
         (2) a corrected setting.

18. The system of item 17, wherein the plurality of instructions, when executed by the at least one processor, cause the at least one processor to apply a random value to the first setting to obtain the randomized setting.

19. The system of item 17 or 18, wherein the plurality of instructions, when executed by the at least one processor, cause the at least one processor to apply a correction factor to the first setting to obtain the corrected setting.

20. The system of any one of items 17 to 19, wherein the second volume of gas is delivered in accordance with a randomized setting if the measured value satisfies the criterion.

21. The system of any one of items 17 to 20, wherein the second volume of gas is delivered in accordance with a corrected setting if the measured value does not satisfy the criterion.

22. The system of any one of items 17 to 21, wherein the ventilator parameter is tidal volume.

23. The system of any one of items 17 to 22, wherein the physiological parameter is esophageal pressure.

24. A method for operating a system to provide ventilation assistance or control, the method comprising:
   (a) causing a processor to receive a first setting for a ventilator parameter and a criterion for a physiological parameter;
   (b) causing a first volume of gas to be delivered to a patient in accordance with the first setting;
   (c) obtaining a measured value for the physiological parameter;
   (d) causing the processor to determine whether the measured value satisfies the criterion; and
   (e) causing a second volume of gas to be delivered to a patient, wherein the second volume of gas is delivered in accordance with (i) a randomized setting or (ii) a corrected setting.

25. The method of item 24, the method further comprising applying a random value to the first setting to obtain the randomized setting.

26. The method of item 24 or 25, the method further comprising applying a correction factor to the first setting to obtain the corrected setting.

27. The method of any one of items 24 to 26, wherein the second volume of gas is delivered in accordance with a randomized setting if the measured value satisfies the criterion.

28. The method of any one of items 24 to 27, wherein the second volume of gas is delivered in accordance with a corrected setting if the measured value does not satisfy the criterion.

29. The method of any one of items 24 to 28, wherein the ventilator parameter is tidal volume.

30. The method of any one of items 24 to 29, wherein the physiological parameter is esophageal pressure.

31. A system for providing ventilation assistance or control, the system comprising:
   (a) at least one processor;
   (b) at least one operator interface configured to provide input to the processor;
   (c) at least one input device; and
   (d) at least one memory device that stores a plurality of instructions, which when executed by the at least one processor, cause the at least one processor to:
      (i) operate with the at least one operator interface to receive an operator generated ventilator setting and a first correction factor;
      (ii) operate with the at least one operator interface to receive a criterion for a physiological parameter;
      (iii) operate with the at least one input device to receive a measured value for the physiological parameter;
      (iv) determine whether the measured value satisfies the criterion; and
      (v) cause a volume of gas to be delivered to a patient, wherein the volume of gas is delivered according to an automatically adjusted ventilator setting.

32. The system of item 31, wherein the plurality of instructions, when executed by the at least one processor, cause the at least one processor to calculate the automatically adjusted ventilator setting by applying the first correction factor to the operator generated ventilator setting.

33. The system of item 31 or 32, wherein the plurality of instructions, when executed by the at least one processor, cause the at least one processor to calculate the automatically adjusted ventilator setting by applying a random value to the operator generated ventilator setting.

34. The system of any one of items 31 to 33, wherein, if the measured value satisfies the criterion, the automatically adjusted ventilator setting is obtained by application of a random value to the operator generated ventilator setting.

35. The system of any one of items 31 to 34, wherein the plurality of instructions, when executed by the at least one processor, cause the at least one processor to adjust the first correction factor to obtain a second correction factor if the measured value does not satisfy the criterion.

36. The system of any one of items 31 to 35, wherein the plurality of instructions, when executed by the at least one processor, cause the at least one processor to calculate the automatically adjusted ventilator setting by application of the second correction factor to the operator generated ventilator setting.

37. The system of any one of items 31 to 36, wherein, if the measured value does not satisfy the criterion, the automatically adjusted ventilator setting is obtained by adjustment of the first correction factor to obtain a second correction factor and application of the second correction factor to the operator generated ventilator setting.

38. The system of any one of items 31 to 37, wherein the physiological parameter is esophageal pressure.

39. A method for operating a system to provide ventilation assistance or control, the method comprising:
(a) causing a processor to receive an operator generated ventilator setting and a first correction factor;
(b) causing the processor to receive a criterion for a physiological parameter;
(c) obtaining a measured value for the physiological parameter;
(d) causing the processor to determine whether the measured value satisfies the criterion; and
(e) causing a volume of gas to be delivered to a patient, wherein the volume of gas is delivered according to an automatically adjusted ventilator setting.

40. The method of item 39, the method further comprising obtaining the automatically adjusted ventilator setting by applying the first correction factor to the operator generated ventilator setting.

41. The method of item 39 or 40, the method further comprising obtaining the automatically adjusted ventilator setting by applying a random value to the operator generated ventilator setting.

42. The method of any one of items 39 to 41, wherein, if the measured value satisfies the criterion, the automatically adjusted ventilator setting is obtained by applying a random value to the operator generated ventilator setting.

43. The method of any one of items 39 to 42, the method further comprising adjusting the first correction factor to obtain a second correction factor if the measured value does not satisfy the criterion.

44. The method of any one of items 39 to 43, the method further comprising obtaining the automatically adjusted ventilator setting by applying the second correction factor to the operator generated ventilator setting.

45. The method of any one of items 39 to 44, wherein, if the measured value does not satisfy the criterion, the automatically adjusted ventilator setting is obtained by adjusting the first correction factor to obtain a second correction factor and applying the second correction factor to the operator generated ventilator setting.

46. The method of any one of items 39 to 45, wherein the physiological parameter is esophageal pressure.

47. The system of any one of items 17 or 38, wherein the criterion for esophageal pressure includes a range or value that is less than 35 cm $H_2O$; alternatively, less than 30 cm $H_2O$; alternatively, less than 25 cm $H_2O$; alternatively, less than 20 cm $H_2O$; or alternatively, less than 10 cm $H_2O$.

48. The system of any one of items 17 or 38, wherein the criterion for esophageal pressure includes a range or value that is between 0 and about 25 cm $H_2O$; alternatively, between about 5 and about 20 cm $H_2O$; or alternatively, between 0 and about 10 cm $H_2O$.

49. The method of any one of items 24 or 46, wherein the criterion for esophageal pressure includes a range or value that is less than 35 cm $H_2O$; alternatively, less than 30 cm $H_2O$; alternatively, less than 25 cm $H_2O$; alternatively, less than 20 cm $H_2O$; or alternatively, less than 10 cm $H_2O$.

50. The method of any one of items 24 or 46, wherein the criterion for esophageal pressure includes a range or value that is between 0 and about 25 cm $H_2O$; alternatively, between about 5 and about 20 cm $H_2O$; or alternatively, between 0 and about 10 cm $H_2O$.

The disclosures of all patents and publications, including published patent applications, are hereby incorporated by reference in their entireties to the same extent as if each patent and publication were specifically and individually incorporated by reference.

It is to be understood that the scope of the present technology is not to be limited to the specific embodiments described above. The present technology may be practiced other than as particularly described and still be within the scope of the accompanying claims.

The presently described technology is now described in such full, clear, concise and exact terms as to enable any person skilled in the art to which it pertains, to practice the same. The foregoing description of the present technology provides illustration and description, but is not intended to be exhaustive or to limit the technology to the precise one disclosed. Modifications and variations are possible in light of the above teachings or may be acquired from practice of the technology. Thus, it is noted that the scope of the invention is defined by the claims and their equivalents. Therefore, it is to be understood that the foregoing describes preferred embodiments of the technology and that modifications may be made therein without departing from the spirit or scope of the invention as set forth in the appended claims and their equivalents.

The invention claimed is:

1. A system for providing ventilation assistance or control, the system comprising:
   (a) at least one processor;
   (b) at least one operator interface configured to provide input to the processor;
   (c) at least one input device; and
   (d) at least one memory device that stores a plurality of instructions, which when executed by the at least one processor, cause the at least one processor to:
      (i) receive, via the at least one operator interface, a first setting for a ventilator parameter and a target pressure for an esophageal pressure of a patient;
      (ii) deliver, via at least one conduit, a first volume of gas to the patient in accordance with the first setting;
      (iii) receive, via the at least one input device, a measured value for the esophageal pressure;
      (iv) determine whether the measured value satisfies the target pressure;
      (v) deliver, via the at least one conduit, a second volume of gas to the patient in accordance with a randomized setting in response to determining that the measured value satisfies the target pressure, the randomized setting determined based on a random value that is applied to the first setting of the ventilator parameter;
      (vi) deliver, via the at least one conduit, the second volume of gas to the patient in accordance with a corrected setting in response to determining that the measured value does not satisfy the target pressure, the corrected setting determined based on a correction factor that is applied to the first setting of the ventilator parameter; and
      (v) adjust the correction factor based upon a magnitude of difference between the measured value and the target pressure of the esophageal pressure of the patient.

2. The system of claim 1, wherein the ventilator parameter is tidal volume.

3. The system of claim 1, wherein the plurality of instructions, when executed by the at least one processor, cause the at least one processor to receive an initial correction factor from a user.

4. The system of claim 3, wherein the plurality of instructions, when executed by the at least one processor, cause the at least one processor to apply the initial correction factor to the first setting before the first volume of gas is delivered to the patient.

5. The system of claim 1, wherein the correction factor includes a value between 0 and 1.5.

6. The system of claim 1, wherein the plurality of instructions, when executed by the at least one processor, cause the at least one processor to adjust the correction factor in a series of iterations at a predetermined rate.

7. The system of claim 1, wherein the target pressure includes a threshold value.

8. The system of claim 1, wherein the target pressure includes a range with a lower limit and an upper limit.

9. The system of claim 1, wherein the at least one input device is selected from a group consisting of an esophageal manometer, a pressure transducer, and a balloon placed in an esophagus of the patient.

10. The system of claim 1, wherein the plurality of instructions, when executed by the at least one processor, cause the at least one processor to determine the measured value from a single measurement collected after a breath of the patient.

11. The system of claim 1, wherein the plurality of instructions, when executed by the at least one processor, cause the at least one processor to determine the measured value from an average of a plurality of measurements continuously collected from the patient.

\* \* \* \* \*